United States Patent [19]

Strahle

[11] Patent Number: Plant 6,896

[45] Date of Patent: Jul. 4, 1989

[54] HYBRID TEA ROSE PLANT 2105-F STRAHLE CULTIVAR

[75] Inventor: Robert Strahle, Carlton, Oreg.

[73] Assignee: Carlton Rose Nurseries, Inc., Carlton, Oreg.

[21] Appl. No.: 171,416

[22] Filed: Mar. 21, 1988

[51] Int. Cl.[4] ..... A01H 5/00

[52] U.S. Cl. ..... Plt./20

[58] Field of Search ..... Plt./20

*Primary Examiner*—Robert E. Bagwill

*Attorney, Agent, or Firm*—Chernoff, Vilhauer, McClung & Stenzel

[57] ABSTRACT

A vigorous rose plant of the hybrid tea class obtained as a seedling from a seed parent entitled "Volare" and a pollen parent entitled "Tonight" provides abundant long-lasting solid velvet red flowers which maintain their true color from flower opening through petal drop on a continuous basis when grown in a greenhouse.

1 Drawing Sheet

BACKGROUND AND SUMMARY OF THE INVENTION

The present invention relates to a new and distinct variety of hybrid tea rose plant, a seedling resulting from a definite effort to produce an improvement of this class of rose. The object of the present invention is to provide a rose plant of the hybrid tea class which is capable of freely yielding quality-cut flowers under greenhouse conditions.

The primary features of this new variety which connotates its distinctive advance over previously existing types is its ability to produce an abundance of solid velvet red flowers which remain true after being cut from when they first open through petal drop from a plant which will continuously yield cut flowers under greenhouse conditions.

The variety of rose plant of the present invention was obtained at Carlton, Oreg. as a seedling from a seed parent entitled "Volare" and a pollen parent entitled "Tonight." The crossing was made in 1980, the first seed of the crossing was sewn in January 1981 and the first flower appeared from these seedlings in April 1981.

Asexual reproduction of this new variety shows that its unique characteristics come true to form and is established and transmitted through succeeding propagations through grafting and budding.

BRIEF DESCRIPTION OF THE DRAWINGS

In the accompanying drawings typically specimens of the vegetative growth and flowers of the new variety are shown in different stages of development and are depicted in color as nearly true as is reasonably possible to make in color illustrations of this character.

FIG. 1 represents a full open flower.

FIG. 2 shows the inside of a petal at the top and the outside of a petal at the bottom.

FIG. 3 shows the flower at the proper stage for cutting.

FIG. 4 shows the bud as the sepals first crack.

FIG. 5 shows upper surface of a compound leaf.

FIG. 6 shows the lower surface of a compound leaf.

FIG. 7 shows a flower with the petals removed.

FIG. 8 shows the cross section of a flower with petals removed exposing the reproductive organs.

FIG. 9 shows flower with petals and stamens removed to expose the pistils.

FIG. 10 shows a typical stem illustrating normal branching and thorn pattern.

DETAILED DESCRIPTION OF THE DISCLOSURE

The following description was made during October 1987 of rose plants of the new and distinct variety growing in a greenhouse at Carlton, Oreg. Color designations are to The Royal Horticulture Society Color Chart.

Flower:

*Flower borne.*—Singly on normal strength, medium long stems.

*Quantity of bloom.*—Abundant in greenhouse.

*Continuity.*—Continuous.

*Fragrance.*—Moderate tea scent.

*Bud.*—Peduncle: medium length; medium weight; erect; light green; almost smooth; few hairs; yellow. Before calyx breaks: Size: small. Form: long pointed without foliaceous appendages on the surface of the bud. As calyx breaks: Color: Red Group 53-B. As first petal opens: Size: small. Form: long pointed. Color: Outside: Red Group 53-C. Inside: Red Group 46-B. Opening: it opens up well.

*Bloom.*—Size when fully open: medium, 2½" to 4". Petalage: double; from 23 to 25 petals; arranged regularly. Form: high centered at first, becoming open; petal tightly cupped inward; becoming later at maturity loosely rolled outward.

*Petals.*—Medium leatherly; with inside velvety; outside satiny. Shape: Outer: round; with flat base. Intermediate: round; with apex flat. Inner: round; with apex flat. Color: Color of newly opened flowers: Outer petal: Outer surface: Red Group 53-C. Inner surface: Red Group 45-B. Intermediate petal: Outside surface: Red Group 53-B. Inside surface: Red Group 45-A. Inner petal: Outside surface: Red Group 53-B.5. Inside surface: Red Group 46-A.5. Color of flower three days after opening: Outer petal: Outside surface: Red Purple Group 60-B. Inner petal: Outside surface: Red Purple Group 58-B. Inside surface: Red Group 45-C.

*General color effect.*—Newly open flower: an overall blending of red color. A little darker on the outside of flower with a satin and velvet mix of texture.

*Flowers three days open.*—Flower is a solid velvet red color once the stamens start to show.

*Behavior.*—Petals persist.

*Flower longevity.*—Cut flowers grown in greenhouse keep at livingroom temperature 9–11 days during October.

Reproductive organs:

*Stamens.*—Many: arranged regularly about pistils. Filaments: many; most with anthers; medium length. Color: red. Anthers: all open at once; small. Color: yellow. Pollen: abundant; yellow. Pistils: many. Styles: even; medium length; medium weight; bunched. Stigma: white. Ovaries: all enclosed in receptacle. Hips: pear-shaped; moderately smooth; walls medium thickness fleshy; russet. Sepals: permanent; medium length; pear-shaped. Seeds: many; medium size.

Plant:

*Foliage.*—Leaves: compound of five leaflets; moderately abundant; medium size; moderately leathery. Leaflets: ovate with apex acuminate, base round, margin simply serratedentate. Color: Mature upper surface: Green Group 137-A. Mature under surface: Yellow Green Group 138-B. Young upper surface: Yellow Green Group 147-A. Young under surface: Greyed-Green Group 191-A. Rachis: medium. Upper side: grooved. Under side: sparsely prickly. Stipules: medium length; narrow; short points; turning out an angle of less than 45 degrees. Disease: subject to mildew; resistance comparable to the average variety growing under the same cultural conditions. Growth: Habit: upright; much branched. Growth: very free, vigorous. Canes: moderately heavy. Main stems: dull. Color: Yellow-green Group 146-A. Prickles: several. Color: Greyed-orange Group 166-D. Hairs: none. Branches: dull. Color: Green Group 138-A. Prickles: several. Color: Greyed-green Group 195-A. Hairs: none. New shoots: bright. Color: Greyed-orange Group 176-B. Prickles: several. Color: Greyed-orange Group 183-B. Hairs: none.

What is claimed is:

1. A new and distinct variety of rose plant of the hybrid tea class obtained as a seedling from a seed parent entitled "Volare" and a pollen parent entitled "Tonight," characterized by its solid velvet red color which is maintained from flower opening through petal drop, and its ability to yield flowers on a continuous basis when grown in a greenhouse, substantially as shown and described.

* * * * *

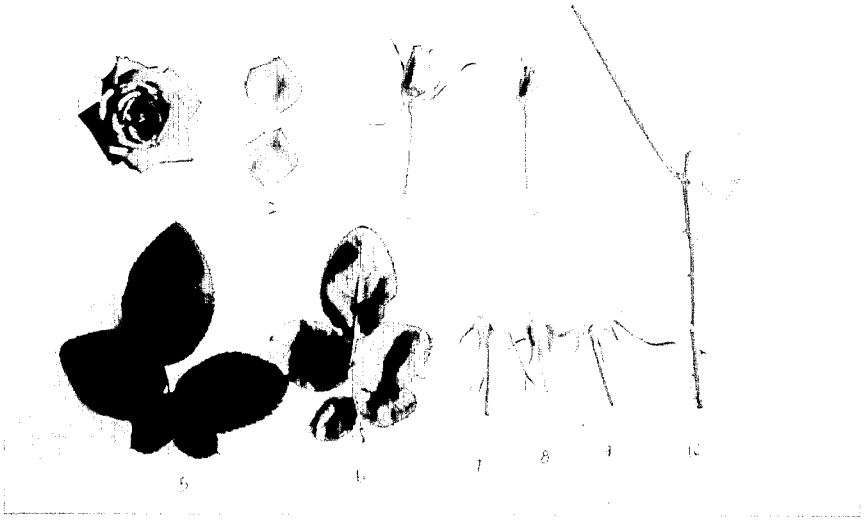
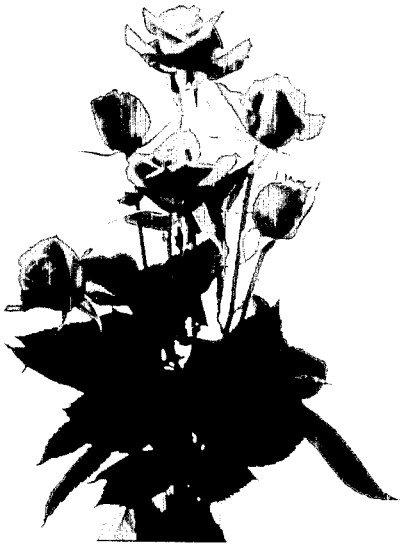
FIG. 11

UNITED STATES PATENT AND TRADEMARK OFFICE

CERTIFICATE OF CORRECTION

PATENT NO. : PP 6,896

DATED : July 4, 1989

INVENTOR(S) : Robert Strahle

It is certified that error appears in the above-identified patent and that said Letters Patent is hereby corrected as shown below:

Col. 1, line 31 Change "typically" to --typical--

Signed and Sealed this

Third Day of March, 1992

*Attest:*

HARRY F. MANBECK, JR.

*Attesting Officer*

*Commissioner of Patents and Trademarks*